United States Patent [19]

Ensminger et al.

[11] Patent Number: 5,053,013
[45] Date of Patent: Oct. 1, 1991

[54] IMPLANTABLE INFUSION DEVICE

[75] Inventors: William D. Ensminger; James A. Knol; James C. Andrews, all of Ann Arbor, Mich.

[73] Assignee: The Regents of the University of Michigan, Ann Arbor, Mich.

[21] Appl. No.: 539,793

[22] Filed: Jun. 18, 1990

Related U.S. Application Data

[63] Continuation-in-part of Ser. No. 487,541, Mar. 1, 1990.

[51] Int. Cl.⁵ ............................................. A61M 5/178
[52] U.S. Cl. .................................. 604/167; 604/175; 604/256
[58] Field of Search .................... 604/167, 175, 93, 86, 604/244, 256, 283, 4, 8-10, 49, 905; 128/DIG. 26

[56] References Cited

U.S. PATENT DOCUMENTS

| | | |
|---|---|---|
| 3,288,137 | 1/1964 | Lund . |
| 3,402,710 | 9/1968 | Paleschuck . |
| 3,565,078 | 2/1971 | Vaillancourt et al. . |
| 3,699,956 | 10/1972 | Kitrilakis et al. . |
| 4,181,132 | 1/1980 | Parks . |
| 4,190,040 | 2/1980 | Schulte . |
| 4,230,109 | 10/1980 | Geiss . |
| 4,256,102 | 3/1981 | Monaco . |
| 4,387,879 | 6/1983 | Tauschinski . |
| 4,430,081 | 2/1984 | Timmermans , |
| 4,439,188 | 3/1984 | Dennehey et al. . |
| 4,447,237 | 5/1984 | Frisch et al. . |
| 4,464,178 | 10/1984 | Dalton . |
| 4,490,137 | 12/1984 | Moukheibir . |
| 4,491,126 | 1/1985 | Cullor . |
| 4,543,088 | 9/1985 | Bootman et al. . |
| 4,547,194 | 10/1985 | Moorehead . |
| 4,569,675 | 2/1986 | Prosl et al. . |
| 4,578,061 | 3/1986 | Lemelson . |
| 4,578,063 | 3/1986 | Inmann et al. . |
| 4,581,020 | 4/1985 | Mittleman . |
| 4,623,329 | 11/1985 | Drobish et al. . |
| 4,634,422 | 1/1987 | Kantrowitz et al. . |
| 4,645,495 | 2/1987 | Vaillancourt . |
| 4,650,473 | 3/1987 | Bartholomew et al. . |
| 4,673,394 | 6/1987 | Fenton, Jr. et al. . |
| 4,682,981 | 7/1987 | Suzuki et al. . |
| 4,692,146 | 9/1987 | Hilger . |

(List continued on next page.)

FOREIGN PATENT DOCUMENTS

| | | |
|---|---|---|
| 0119596 | 3/1984 | European Pat. Off. . |
| 134745 | 8/1984 | European Pat. Off. . |
| 3528878 | 2/1987 | Fed. Rep. of Germany . |
| 5288787 | 2/1987 | Fed. Rep. of Germany . |

OTHER PUBLICATIONS

Rational Drug Therapy, May, 1988, vol. 22, No. 5, William D. Ensminger M.D. and Ira S. Wollner, M.D.

Primary Examiner—John D. Yasko
Attorney, Agent, or Firm—Harness, Dickey & Pierce

[57] ABSTRACT

In infusion port for implantation within a patient for providing repeated access to specific tissue within a patient and communicating with the tissue by an internal implanted catheter. The infusion port in accordance with this invention includes a housing having a funnel shaped inlet orifice which terminates in a reduced diameter guide passageway. Installed within the housing is an articulating catheter valve such as a leaflet valve assembly. The housing communicates with an exit passageway which is attached to an internal outflow catheter coupling the infusion port to a specific tissue within the patient. In use, a needle is used to penetrate the patient's skin and contacts the entrance orifice of the infusion port. The entrance orifice guides the needle point into alignment with and into the guide passageway. The guide passageway targets a small portion of the articulating catheter valve which can be in the form of a leaflet valve assembly. Once through the catheter valve, fluids may be infused into the patient through the needle or withdrawn from the patient. Alternatively, an external catheter or other filament can be placed in communication with the outflow catheter by feeding it in into the infusion port and into the implanted catheter after being introduced over a needle which is restricted from entering the implanted catheter.

37 Claims, 2 Drawing Sheets

U.S. PATENT DOCUMENTS 4,695,273 9/1987 Brown .
4,704,103 11/1987 Stober et al. .
4,710,167 12/1987 Lazorthes .
4,710,174 12/1987 Moden et al. .
4,712,583 12/1987 Pelmulder et al. .
4,781,693 11/1988 Martinez et al. .
4,781,695 11/1988 Dalton .
4,810,241 3/1989 Rogers .
4,842,591 6/1989 Luther .
4,857,053 8/1989 Dalton .
4,857,062 8/1989 Russell ........................ 604/256
4,886,501 12/1989 Johnston et al. .

IMPLANTABLE INFUSION DEVICE

CROSS REFERENCE TO RELATED APPLICATION

This application is a continuation-in-part of application Ser. No. 487,541 filed on Mar. 1, 1990 pending a title common with this application.

BACKGROUND AND SUMMARY OF THE INVENTION

This invention relates to a device for infusing a therapeutic agent to a desired site within a patient or withdrawing a fluid from a patient, and more particularly, to such a device which is implanted such that no portion is transcutaneous. Its access portion is subcutaneous but designed so as to facilitate repeated access by the percutaneous route.

In current human and animal medical practice, there are numerous instances where therapeutic agents must be delivered to a specific organ or tissue within the body. An example is the infusion of chemotherapy into a central vein on a recurring basis over a lengthy treatment period for widespread sites of malignant tumor. Without an infusion device for intravenous drug infusion, multiple vein punctures over a lengthy period results in progressive thrombosis, venous sclerosis, and destruction of small diameter peripheral vessels. In other cases, it may be desirable to infuse chemotherapy to a localized malignant tumor site. It may be difficult or impossible to deliver an agent specifically to such a site on a regular repetitive basis without surgically implanting an infusion system. Similarly, repeated arterial access is occasionally needed for injection of an X-ray dye or contrast agent into an artery for diagnostic purposes. In other situations, there is a need to remove a body fluid repetitively for analysis from a remote body site. Finally, sensing and physiological measuring devices incorporated into small diameter catheters and small diameter optical fibers are increasingly being utilized for monitoring body processes and could be more easily implemented through a properly designed access device with an adequate internal diameter.

In prior medical practice, percutaneous catheters have been used to provide vascular or organ access for drug therapy or removing body fluids. Although such systems generally performed in a satisfactory manner, numerous problems were presented by such therapy approaches, including the substantial care requirements by patients, e.g. dressing changes with sterile techniques, a significant rate of infection of the catheter because of its transcutaneous position, and a high rate of venous thrombosis, particularly if the catheter was located within an extremity vein.

Implantable infusion devices or "ports" have recently become available and are a significant advance over transcutaneous catheters. Presently available infusion ports have a number of common fundamental design features. The ports themselves comprise a housing which forms a reservoir which can be constructed from a variety of plastic or metal materials. A surface of the reservoir is enclosed by a high-density, self-sealing septum, typically made of silicone rubber. Connected to the port housing is an outflow catheter which communicates with a vein or other site within the patient where it is desired to infuse therapeutic agents. Implantation of such devices generally proceeds by making a small subcutaneous pocket in the patient under local anesthesia. The internal outflow catheter is tunneled to the desired infusion site and is connected to the infusion port. When the physician desires to infuse or remove material through the port, a hypodermic needle is used which pierces the skin over the infusion port and is placed into the port.

Although presently available implantable infusion ports generally operate in a satisfactory manner, they have a number of shortcomings. Since these devices rely on a compressed rubber septum for sealing, there are limitations in the diameter of needles which can be used to penetrate the septum, since large diameter needles can seriously damage the septum. Moreover, the needles used must be of a special design which minimizes septum damage. These diameter limitations severely restrict the flow rate of fluids passing through the port.

For prolonged infusion using a conventional port, the infusion needle is taped to the patients skin to hold it in position. Conventional ports do not allow the needle to penetrate deeply into the port so that a small displacement of the needle can cause it to be pulled from the port. In cases where locally toxic materials are being infused, extravasation of such materials can cause local tissue damage which can lead to a requirement for corrective surgery such as skin grafting or removal of tissue.

Presently available implantable drug infusion devices must also have a significant size to provide an acceptable target surface area for the physician who must locate the port and penetrate the septum properly with a needle. The port housing becomes bulky as the septum size increases since structure is required to maintain the septum in compression to provide self-sealing after the needle is removed. Moreover, presently available infusion ports are difficult to clear if thrombosis occurs within them or in the implanted outflow catheter, since it is difficult if not impossible to feed a cleaning wire through the penetrating hypodermic needle in a manner which will clear the infusion device and the internal outflow catheter. Present infusion ports have a retained volume beneath the self-sealing septum which increases the volume of drug which must be administered to enable a desired quantity to reach the infusion site. This retained volume also poses problems when a physician desired to deliver different drugs to the same infusion site which are incompatible when mixed. In addition, when it is desired to withdraw blood through the port, the retained volume of the prior art infusion ports is an area where blood clotting can occur, thus interfering with future access to the site. And finally, for present infusion ports, there is a risk that the physician attempting to pierce the port septum will not properly enter it, leading to the possibility of extravasation which can cause significant undesirable consequences as mentioned previously.

The present invention relates to an implantable infusion port which provides numerous enhancements over prior art devices. In accordance with this invention, an infusion port is provided which incorporates the funnel-shaped entrance orifice which narrows down to a reduced diameter guide passageway. The guide passageway terminates at an internal cavity which retains an articulating catheter valve such as a multi-element leaflet valve assembly. The port also has an exit passageway which connected to an implanted outflow catheter. The infusion port of the present invention is adapted to be used in conjunction with a sharp hypodermic access needle of conventional design which may be used by itself for infusion or fluid withdrawal, or with an external inflow catheter having the needle fed through it (or vise versa) allowing a catheter to be put in position within the infusion port or fed into the implanted catheter for infusion or withdrawal of fluid. The entrance orifice guides the needle to the guide passageway. The reduced diameter guide passageway of the port housing accurately aligns the access needle to strike the catheter valve at a desired area so that a needle can be used to penetrate the catheter valve repeatedly without impairing the function of the valve. Various forms of articulating catheter valves can be employed in connection with the present invention. One such valve is a leaflet valve having one or more flat discs of an elastomeric material having cuts through them to define leaves or flaps which normally resist the flow of fluids across the valve, but can be penetrated by a sharp access needle.

Use of the embodiment of this application differs from those of the parent application in that it is primarily intended to be used with a sharp access needle as compared with the embodiments of the parent application which are intended to be used with a blunt accessing instrument.

The convenient access to the port and internal outflow catheter provided by this invention enables these elements to be cleared with a wire, avoiding the problem of permanent impaction of prior art devices. In addition, the ability to feed a guide wire into the infusion port and internal catheter of this invention enables the internal catheter to be repositioned using a bent or "steerable" guide wire.

The infusion ports having an articulating catheter valve of this invention possess the advantage that they have a very small reservoir or "dead space", meaning that virtually all of the infused fluid is throughput to the desired infusion site. This invention, therefore, facilitates infusion of incompatible materials in a serial fashion since very little of the previously infused fluid remains in the device when a subsequent infusion is carried out. The port of this invention also permits an introduced catheter or other filament to be deeply inserted into the internal outflow catheter which reduces the possibility of small displacement of the introduced filament causing it to be from being withdrawn from the port during infusion.

Additional benefits and advantages of the present invention will become apparent to those skilled in the art to which this invention relates from the subsequent description of the preferred embodiments and the appended claims, taken in conjunction with the accompanying drawings.

DETAILED DESCRIPTION OF THE INVENTION

Figure 1:
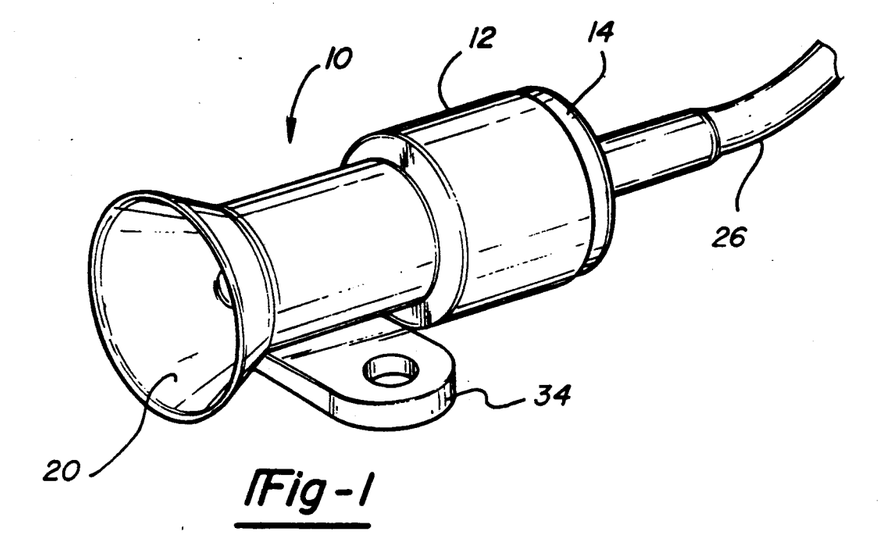
FIG. 1 is a pictorial view of an infusion port in accordance with this invention shown attached to a internal catheter.

An infusion port in accordance with this invention is shown in FIG. 1 and is generally designated there by reference number 10. Infusion port 10 principally comprises housing 12, outlet plug 14, and articulating valve assembly 16.

Figure 4:
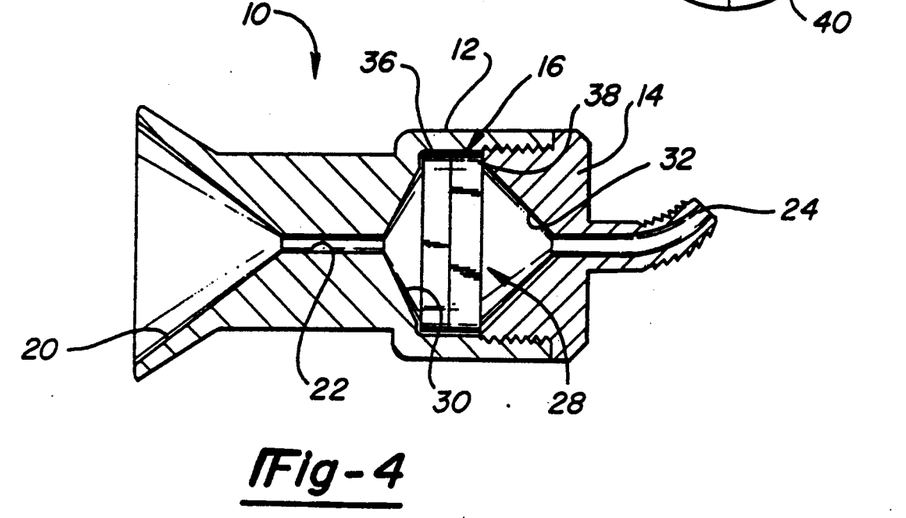
FIG. 4 is a cross-sectional view taken along lines 4—4 of FIG. 1 showing the internal construction of the infusion port according to this invention.

As best shown in FIGS. 1 and 4, housing 12 defines a funnel-shaped entrance orifice 20, the function of which is to guide an access needle 18 toward its center. Although orifice 20 is shown in the shape of a circular cone, other configurations could be used such as elliptical or flattened cones could be used to define the orifice opening. Such alternative shapes could be used to decrease the profile height of the device. Any configurations used for orifice 20 must posses a decreasing cross-sectional area for the purpose of guiding the access needle to a focus point. At the base of the orifice cavity shown in the Figure is a reduced diameter guide passageway 22. Guide passageway 22 is straight and has a diameter only slightly greater than a diameter of elements which are desired to be passed into port 10.

Figure 2:
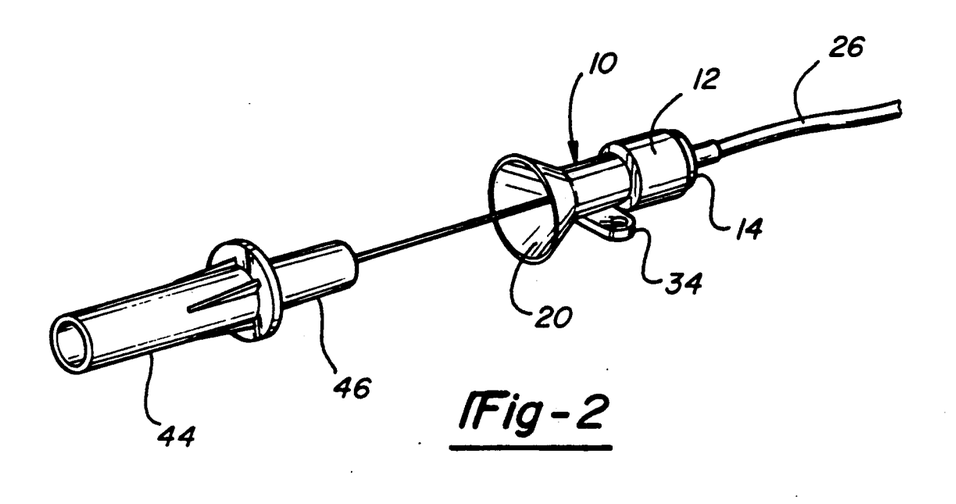
FIG. 2 illustrates an access needle with an external catheter being used to penetrate the infusion port shown in FIG. 1.
Figures 3, 5:
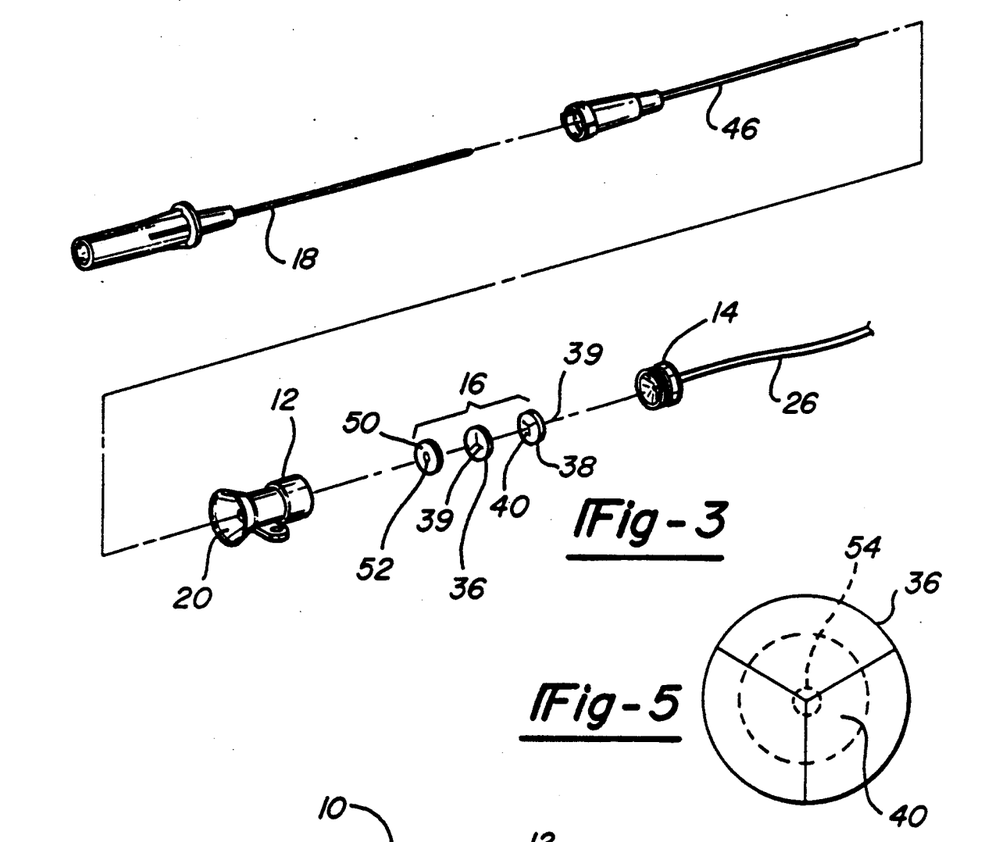
FIG. 3 is an exploded pictorial view of the infusion port of this invention shown in FIG. 2 shown with an optional elastic sealing disc for use with the leaflet valve elements.
FIG. 5 is a frontal view of the elastic leaflet valve elements as shown in FIGS. 3 and 4.

Outlet plug 14 is externally threaded which enables it to be attached to the end of housing 12 opposite entrance orifice 20. Outlet plug 14 defines an externally barbed projecting hollow post 24 which enables an internal outflow catheter 26 to be slid onto the post and attached to the infusion port as shown in FIGS. 1, 2 and 3. Hollow post 24 can be intentionally bent as shown in FIG. 4 to prevent needle 18 from passing entirely through the device in which case it could damage outflow catheter 26. As is best shown in FIG. 4, once assembled together, housing 12 and outlet plug 14 define an internal cavity which accommodates leaflet valve assembly 16. As shown in FIG. 4, cavity 28 defines a pair of conical surfaces, with conical surface 30 joining with guide passageway 22 and conical surface 32 joining with exit plug post 24.

Mounting plate 34 is attached to housing 12 or and provides a means of mounting infusion port 10 to support tissues within a patient using sutures, surgical staples, etc.

Leaflet valve assembly 16 shown in the illustrated embodiment of this invention includes a pair of elastic leaflet valve discs 36 and 38. Each of the elastic discs include slits extending from their geometric center and radially outward toward the perimeter of the elastic disc to define three separate flaps or leaves 40. Elastic discs 36 and 38 are stacked against one another in a manner to disalign cuts 39 so that the leaves 40 of each disc overlies the cuts in the other to enhance the sealing characteristic of the leaflet valve assembly. As shown in FIG. 4, when housing 12 and outlet plug 14 are assembled together, the outer periphery of elastic discs 36 and 38 are slightly compressed to provide a seal which prevents fluids from leaking around the outer edges of the elastic disc elements.

FIG. 3 shows an optional disc valve element 50 (not shown in FIG. 4) which is provided to further enhance the sealing characteristics of valve assembly 16. Disc element 50 has a hole 52 through its center, which has a diameter slightly smaller than the needle or catheter which port 10 is designed to accommodate. Valve element 50 is positioned to be the first element encountered by the access needle. This orientation provided to prevent the apexes of leaves 40 from damaging valve disc 50 or interfering with its sealing capability.

Infusion port 10 in accordance with this invention is adapted to be accessed using a conventional hypodermic needle 18 with a sharp end, which can be hollow or solid depending on the intended application. Needle 18 can be used by itself or with an external catheter 46, which the needle is slid through so that the needle and catheter combination can be pierced through the skin and positioned into port 10 allowing the needle to be later withdrawn, leaving catheter 46 inside port 10 to provide fluid flow into or from the patient. The introduced catheter 46 can be threaded into outflow catheter 26 to any extent desired, preventing unintentional withdrawal of the introduced catheter.

FIG. 2 shows infusion port 10 being accessed by a needle 18 and catheter 46 combination. When the physician desires to access port 10, needle 18 is used to pierce the patient's skin at an area adjacent the port entrance orifice 20 and the needle is pushed into the port. Entrance orifice 20 receives the sharp end of needle 18 and guides it toward and into guide passageway 22. The guide passageway then orients needle 18 and aims it to strike leaflet valve assembly 16 at the center of valve elements 36 and 38, which is the point of intersection of the cuts 39 defining leaves or flaps 40. Guide passageway 22, therefore, guides needle 18 to strike leaflet valve assembly 16 in an area where cutting or damage to the elastic disc elements is minimized since the discs are most easily penetrated at their central region where their flexibility is greatest. Elastic discs 36 and 38 are intentionally provided with three or more leaves or flaps since it is believed that a leaflet valve having a single slit defining only two leaves may not provide an acceptable resistance to damage by the penetrating needle. Such susceptibility to damage could occur since such a valve configuration is not believed to provide flaps with sufficient resiliency to bend away from the introduced needle, but would instead tend to be engaged and penetrated by the inserted needle 18, leading to the potential for physical damage to the disc elements.

In order to provide an acceptable resistance to damage of valve assembly 16 by needle 18, it is believed that the diameter of passageway 22 which is superimposed on disc 36 in FIG. 5 and designated by reference number 54, should be no larger than one-half the diameter of the slit portion of elastic discs 36 and 38 which is encompassed by a circle designated as diameter 56. Passageway diameters 54 greater than that ratio would permit a penetrating needle with its sharp point to strike the leaflet valve assembly 16 at near its outer perimeter, where leaves 40 are not as supple and are more likely to be pierced by the access needle than the center portion. Controlling the position of penetration of needle 18 also protects elastic disc 50 from damage which would occur if the needle struck outside of hole 52.

The conical surfaces 30 and 32 of valve cavity 28 are provided to accommodate the flexing of valve leaves 40 in both directions. When access needle 18 is inserted into infusion port 10, the leaves 40 are permitted to deflect toward hollow post 24. In addition, conical cavity 32 insures that the access needle 18 or other introduced filament is properly guided to pass through hollow post 24 and into internal outflow catheter 26, if desired. Upon withdrawal of access needle 18 or catheter 46 from infusion port 10, conical surface 30 enables the leaves 40 of valve assembly 16 to be freely deflected in an opposite direction.

During the step of inserting needle 18 into port 10, a positive indication of full insertion is felt by the attending physician as needle 18, which is relatively rigid, engages the bent portion of hollow post 24. This stop is provided to prevent accidental damage to outflow catheter 26. However, the introduced filament or catheter 46 which is more flexible than access needle 18 can be readily threaded past hollow post 24 to provide deep insertion.

In addition to permitting the insertion of a needle 18 and catheter 46 to port 10, this invention would allow a guidewire to be introduced into the port through access needle 18 which could be fed through the device and into and through the internal outflow catheter 46 to remove thrombosis or other clogging problems. Various other filaments type elements could also be used with port 10 such as optical fibers, electrical conductors, remote sensing systems, etc.

Numerous materials may be used to form the elements of this invention. Since housing 12 will be subject to being struck by sharp needles which must be redirected into guide passageway 22, it is desirable to form the housing of a hard metal material such as stainless steel or titanium. Soft materials, if used to form entrance orifice 20 could be subject to being gouged by needle 18, preventing proper guiding of the access needle. Similarly, exit outlet plug 14 is subject to being struck by a sharp needle and should also be made of a hard metal material for the reasons mentioned in connection with housing 12. Elastic discs 36, 38 and 50 can be made of numerous elastic materials such as silicone rubber.

While the above description constitutes the preferred embodiments of the present invention, it will be appreciated that the invention is susceptible of modification, variation and change without departing from the proper scope and fair meaning of the accompanying claims.

We claim:

1. An implantable patient access device for permitting access to an implanted internal catheter using a needle and enabling the introduciton of a flexible filament such as an external catheter, wire or optical fiber, comprising:

housing means defining a entrance orifice having a decreasing cross-sectional area and having a surface formed of a hard material for guiding said needle upon contacting said entrance orifice into a guide passageway within said housing means, said housing means further defining an exit orifice for attachment of said internal catheter, an articulating catheter valve within said housing means which normally remains closed to provide resistance to flow of fluids through said valve, yet opens when penetrated by said needle enabling said needle to communicate with said internal catheter wherein said guide passageway guides and orients said needle to strike said catheter valve at a predetermined area, and mounting means formed by said housing means for affixing said housing means subcutaneously.

2. An implantable patient access device according to claim 1 wherein said catheter valve comprises a leaflet valve having at least two elastic disc elements stacked together.

3. An implantable patient access device according to claim 2 wherein said disc elements having slits therethrough and each defining three or more deflectable valve leaves and wherein said guide passageway causes said needle to strike said disc elements at near the geometric center of said cuts.

4. An implantable patient access device according to claim 3 wherein said disc elements are stacked together such that said slits of a first of said disc element are not aligned with said slits of a second of said disc elements.

5. An implantable patient access device according to claim 3 wherein said guide passageway has a diameter not greater than one-half of the diameter of said elastic disc element portions defining said leaves.

6. An implantable patient access device according to claim 2 wherein said housing means further defines an internal cavity within which said leaflet valve is disposed.

7. An implantable patient access device according to claim 6 wherein said internal cavity provides clearance for said valve leaves to deflect toward said exit orifice.

8. An implantable patient access device according to claim 6 wherein said internal cavity provides clearance for said valve leaves to deflect toward said entrance orifice.

9. An implantable patient access device according to claim 6 wherein said housing means is defined by a main housing defining said entrance orifice and said guide passageway and an outlet plug connected with said main housing defining said exit orifice, said main housing and said outlet plug cooperating to define said internal cavity.

10. An implantable patient access device according to claim 1 wherein said housing means defines means to limit the amount of penetration of said needle in said housing means while allowing more flexible introduced filaments to be threaded entirely through said access device.

11. An implantable patient access device according to claim 10 wherein said means to limit the amount of penetration comprises a curved passageway which defines the limit of said penetration.

12. An implantable patient access device according to claim 2 wherein said leaflet valve further comprises a disc element having a hole for sealing against said filament.

13. An implantable patient access device according to claim 12 wherein said disc element having a hole is placed such that said needle passes through said element with a hole before passing through said leaflet valve elastic disc elements.

14. An implantable patient access device according to claim 1 further comprising an external catheter having said needle inserted into its hollow core and said access device allowing the combination of said needle and said external catheter to be inserted into said access device and thereafter allowing said needle to be removed leaving said external catheter inside said access device.

15. An implantable patient access device for communicating to a desired tissue site within the patient through an implanted internal catheter and accessible using a needle for enabling the introduction of a flexible filament such as an external catheter, wire or optical fiber, comprising:
  a housing defining a entrance orifice having a decreasing cross-sectional area and having a surface formed of a hard material for guiding said needle upon contacting said entrance orifice into a straight guide passageway within said housing, and defining an internal cavity communicating with said guide passageway and an exit orifice,
  a leaflet valve assembly positioned within said internal cavity and including at least two elastic disc elements stacked together, each of said disc elements having slits formed therethrough and defining a plurality of deflectable valve leaves, said disc elements stacked together such that said slits in each of said disc elements are not aligned with said slits of the adjacent of said disc elements, and
  mounting means formed by said housing for affixing said housing subcutaneously.

16. An implantable patient access device according to claim 15 wherein said disc elements define three or more valve leaves.

17. An implantable patient access device according to claim 15 wherein said guide passageway has a diameter not greater than one-half of the diameter of said elastic disc element portions defining said leaves.

18. An implantable patient access device according to claim 15 wherein said housing internal cavity provides clearance for said valve leaves to deflect toward said exit orifice.

19. An implantable patient access device according to claim 15 wherein said housing internal cavity provides clearance for said valve leaves to deflect toward said entrance orifice.

20. An implantable patient access device according to claim 15 wherein said housing includes a main housing defining said entrance orifice and said guide passageway and an outlet plug connected with said main housing defining said exit orifice, said main housing and said outlet plug cooperating to define said internal cavity.

21. An implantable patient access device according to claim 15 wherein said leaflet valve further comprises a disc element having a hole for sealing against an introduced filament.

22. An implantable patient access device according to claim 21 wherein said disc element having a hole is placed such that said needle passes through said element with a hole before passing through said leaflet valve elastic disc elements.

23. An implantable patient access device according to claim 15 wherein said housing defines means to limit the amount of penetration of said needle in said housing while allowing said flexible introduced filaments to be threaded entirely through said access device.

24. An implantable patient access device according to claim 23 wherein said means to limit the amount of penetration comprises a curved passageway which defines said limit of penetration.

25. An implantable patient access device according to claim 24 wherein said curved passageway allows said filament to be pushed through said curved passageway and into said implanted internal catheter.

26. An implantable patient access device according to claim 15 wherein said needle is placed through the hollow core of an external catheter and placed into said access device as a combination and wherein said needle may be withdrawn leaving said external catheter inside of said access device.

27. An implantable patient access device according to claim 15 wherein said needle allowing said filament to be fed into said access device after being introduced into said access device by said needle.

28. An implantable patient access device for infusion or withdrawal of a fluid through an implanted internal catheter communicating said device with a preselected site within the patient and accessible using a needle, comprising:

housing means defining a entrance orifice having a decreasing cross-sectional area for guiding said needle into a guide passageway within said housing means, said housing means further defining an exit orifice for attachment of said internal catheter and an internal cavity, and a leaflet valve having at least two elastic disc elements stacked together within said housing internal cavity which normally remains closed to provide resistance to flow of fluids through said valve, yet opens when penetrated by said needle enabling said needle to communicate with said internal catheter wherein said guide passageway guides and orients said needle to strike said leaflet valve at a predetermined area, said internal cavity providing clearance for said valve leaves to deflect toward said exit orifice.

29. An implantable patient access device for infusion or withdrawal of a fluid through an implanted internal catheter communicating said device with a preselected site within the patient and accessible using a needle, comprising:

housing means defining a entrance orifice having a decreasing cross-sectional area for guiding said needle into a guide passageway within said housing means, said housing means further defining an exit orifice for attachment of said internal catheter and an internal cavity, and a leaflet valve having at least two elastic disc elements stacked together within said housing internal cavity which normally remains closed to provide resistance to flow of fluids through said valve, yet opens when penetrated by said needle enabling said needle to communicate with said internal catheter wherein said guide passgeway guides and orients said needle to strike said leaflet valve at a predetermined area and wherein said internal cavity providing clearance for said valve leaves to deflect toward said entrance orifice.

30. An implantable patient access device for infusion for withdrawal of a fluid through an implanted internal catheter communicating said device with a preselected site within the patient and accessible using a needle, comprising:

housing means defining a entrance orifice having a decreasing cross-sectional area for guiding said needle into a guide passageway within said housing, said housing means further defining an exit orifice for attachment of said internal catheter, said housing defining means to limit the amount of penetration of said needle in said housing while allowing more flexible filaments or catheters to be threaded entirely through said infusion device, and an articulating catheter valve within said housing means which normally remains closed to provide resistance to flow of fluids through said valve, yet opens when penetrated by said needle enabling said needle to communicate with said internal catheter wherein said guide passageway guides and orients said needle to strike said catheter valve at a predetermined area.

31. An implantable patient access device according to claim 30 wherein said means to limit the amount of penetration comprises a curved passageway which defines said limit of penetration.

32. An implantable patient access device communicating to a desired tissue site within the patient by an implanted internal catheter and accessible using a needle for enabling the infusion or withdrawal of fluid through the needle or through an introduced external catheter, comprising:

a housing defining a entrance orifice having a decreasing cross-sectional area for guiding said needle into a straight guide passageway within said housing, and defining an internal cavity communicating with said guide passageway and an exit orifice, and a leaflet valve assembly positioned within said internal cavity and including at least two elastic disc elements stacked together, each of said disc elements having slits formed therethrough each defining a plurality of deflectable valve leaves, said disc elements stacked together such that said slits in each disc are not aligned with said slits of the adjacent of said discs and said housing internal cavity providing clearance for said valve leaves to deflect toward said exit orifice.

33. An implantable patient access device communicating to a desired tissue site within the patient by an implanted internal catheter and accessibly using a needle for enabling the infusion or withdrawal of fluid through the needle or through an introduced external catheter, comprising:

a housing defining a entrance orifice having a decreasing cross-sectional area for guiding said needle into a straight guide passageway within said housing, sand defining an internal cavity communicating with said guide passageway and an exit orifice, and a leaflet valve assembly positioned within said internal cavity and including at least two elastic disc elements stacked together, each of said disc elements having slits formed therethrough each defining a plurality of deflectable valve leaves, said disc elements stacked together such that said slits in each disc are not aligned with said slits of the adjacent of said discs, said housing assembly internal cavity providing clearance for said valve leaves to deflect toward said entrance orifice.

34. An implantable patient access device communicating to a desired tissue site within the patient by an implanted internal catheter and accessible using a needle for enabling the infusion or withdrawal of fluid through the needle or through an introduced external catheter, comprising:

a housing defining a entrance orifice having a decreasing cross-sectional area for guiding said needle into a straight guide passageway within said housing, and defining an internal cavity communicating with said guide passageway and an exit orifice, said housing defining means to limit the amount of penetration of said needle in said housing while allowing more flexible introduced filaments or catheters to be threaded entirely through said device, and a leaflet valve assembly positioned within said internal cavity and including at least two elastic disc elements stacked together, each of said disc elements stacked together such that said slits in each disc are not aligned with said slits of the adjacent of said discs.

35. An implantable patient access device according to claim 34 wherein said means to limit the amount of penetration comprises a curved passageway which defines the said limit of penetration.

36. An implantable patient access device according to claim 35 wherein said curved passageway allows said external catheter to be pushed through said curved passageway and into said implanted internal catheter.

37. An implantable patient access device for permitting access to an implanted internal catheter using a needle and enabling the introduction of a flexible filament such as an external catheter, wire or optical fiber comprising:

housing means defining a entrance orifice having a decreasing cross-sectional area and having a surface formed of a hard material for guiding said needle upon contacting said entrance orifice toward a guide passageway within said housing, said housing means further defining an exit orifice for connection to said internal catheter, an articulating catheter valve within said housing means which normally remains closed to provide resistance to flow of fluids through said valve, yet opens for engagement with said filament enabling said filament to communicate with said internal catheter, and mounting means formed by said housing means for affixing said housing subcutaneously.

* * * * *

UNITED STATES PATENT AND TRADEMARK OFFICE
CERTIFICATE OF CORRECTION

PATENT NO. : 5,053,013

DATED : October 1, 1991

INVENTOR(S) : Ensminger et al.

It is certified that error appears in the above-identified patent and that said Letters Patent is hereby corrected as shown below:

Column 6, line 42, Claim 1,
please change "introduciton" to read --introduction--.

Column 9, line 35, Claim 29,
please change "passgeway" to read --passageway--.

Column 10, line 29, Claim 33,
please change "sand" to read --and--.

Signed and Sealed this

First Day of June, 1993

Attest:

MICHAEL K. KIRK

Attesting Officer

Acting Commissioner of Patents and Trademarks